(12) United States Patent
Bendix et al.

(10) Patent No.: US 10,485,920 B2
(45) Date of Patent: Nov. 26, 2019

(54) NEEDLE UNIT WITH A LOCKABLE NEEDLE SHIELD AND AN INJECTION DEVICE COMPRISING SUCH A NEEDLE UNIT

(71) Applicant: Novo Nordisk A/S, Bagsvaerd (DK)

(72) Inventors: Klaus Bendix, Vanloese (DK); Soeren Kjellerup Hansen, Fjenneslev (DK); Bastian Gaardsvig Kjeldsen, Hilleroed (DK); Mads Schenstroem Stefansen, Copenhagen OE (DK)

(73) Assignee: Novo Nordisk A/S, Bagsvaerd (DK)

( * ) Notice: Subject to any disclaimer, the term of this patent is extended or adjusted under 35 U.S.C. 154(b) by 178 days.

(21) Appl. No.: 15/536,239

(22) PCT Filed: Jan. 8, 2016

(86) PCT No.: PCT/EP2016/050302
§ 371 (c)(1),
(2) Date: Jun. 15, 2017

(87) PCT Pub. No.: WO2016/110580
PCT Pub. Date: Jul. 14, 2016

(65) Prior Publication Data
US 2017/0340807 A1 Nov. 30, 2017

(30) Foreign Application Priority Data
Jan. 8, 2015 (EP) .................................. 15150509

(51) Int. Cl.
*A61M 5/00* (2006.01)
*A61M 5/32* (2006.01)
(Continued)

(52) U.S. Cl.
CPC .......... *A61M 5/002* (2013.01); *A61M 5/3202* (2013.01); *A61M 5/326* (2013.01);
(Continued)

(58) Field of Classification Search
CPC .. A61M 5/3271; A61M 5/3257; A61M 5/321; A61M 5/3243; A61M 5/326; A61M 5/3232; A61M 2005/2073
(Continued)

(56) References Cited

U.S. PATENT DOCUMENTS

| 4,921,491 A | 5/1990 | Champ |
| 5,609,577 A | 3/1997 | Haber et al. |

(Continued)

FOREIGN PATENT DOCUMENTS

| DE | 102004063603 A1 | 7/2006 |
| DE | 102006029911 A1 | 1/2008 |

(Continued)

*Primary Examiner* — Brandy S Lee
*Assistant Examiner* — Nidah M Hussain
(74) *Attorney, Agent, or Firm* — Wesley Nicolas

(57) ABSTRACT

A needle unit (20) comprising: a needle hub (21) comprising a needle (23) and a needle shield (22), wherein the needle hub (21) and the needle shield (22) are arranged to form a needle unit (20) where the needle hub is arranged displaceably inside the needle shield such that the needle hub is displaceable along an axis which is parallel with the longitudinal axis of the needle (23) between a shielded position and an exposed position. The needle hub (21) further comprises a first hub locking element (24) and a second hub locking element (26) and the needle shield (22) further comprises a first shield locking element (25) and a second shield locking element (27), said first hub locking element (24) and said first shield locking element (25) engaging each other in the shielded position to establish a first releasable locking mechanism (24, 25) between the needle hub (21) and the needle shield (22), said second hub locking element (26) and said second shield locking element (27) engaging each other in the shielded position to establish a second locking mechanism (26, 27) between the needle hub (21) and the needle shield (22), both the first and second locking (Continued)

mechanisms (24, 25, 26, 27) being arranged as shock proof locks, and where the first releasable lock mechanism (24, 25) is arranged to engage with the lock release element (31) of the injection device (1) when the needle unit (20) is coupled to the injection device, said engagement allowing the first releasable lock mechanism (24, 25) to be unlocked. The invention further provides an injection device comprising the needle unit and a method of assembling an injection device with the needle unit.

15 Claims, 10 Drawing Sheets

(51) Int. Cl.
*A61M 5/20* (2006.01)
*A61M 5/24* (2006.01)

(52) U.S. Cl.
CPC ......... *A61M 5/3293* (2013.01); *A61M 5/2033* (2013.01); *A61M 2005/247* (2013.01); *A61M 2005/3247* (2013.01)

(58) Field of Classification Search
USPC .......................................... 604/263
See application file for complete search history.

(56) References Cited

U.S. PATENT DOCUMENTS

| | | | |
|---|---|---|---|
| 6,743,203 | B1 | 6/2004 | Pickhard |
| 7,534,229 | B2* | 5/2009 | Hommann ............ A61M 5/326 604/198 |
| 9,138,546 | B2* | 9/2015 | Schubert ............... A61M 5/326 |
| 2004/0193110 | A1 | 9/2004 | Giambattista et al. |
| 2010/0114035 | A1* | 5/2010 | Schubert .............. A61B 5/1444 604/198 |
| 2012/0041373 | A1* | 2/2012 | Bruehwiler ........... A61M 5/002 604/173 |
| 2012/0179110 | A1 | 7/2012 | Gratwohl et al. |
| 2013/0218093 | A1 | 8/2013 | Markussen et al. |
| 2017/0136192 | A1* | 5/2017 | Stefansen ........... A61M 5/2033 |

FOREIGN PATENT DOCUMENTS

| | | |
|---|---|---|
| EP | 0586199 A1 | 3/1994 |
| WO | 2008/077706 A1 | 7/2008 |
| WO | 2012025639 A1 | 3/2012 |
| WO | 2013070789 A2 | 5/2013 |
| WO | 2015150578 A1 | 10/2015 |
| WO | 2015197866 A1 | 12/2015 |
| WO | 2015197867 A1 | 12/2015 |

\* cited by examiner

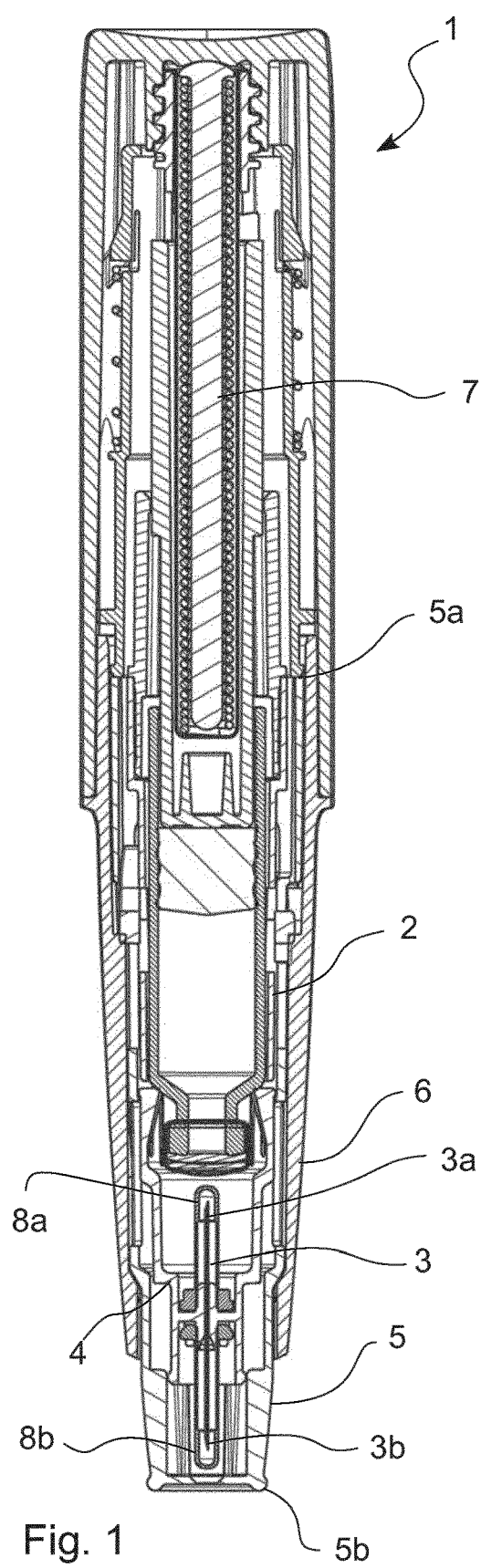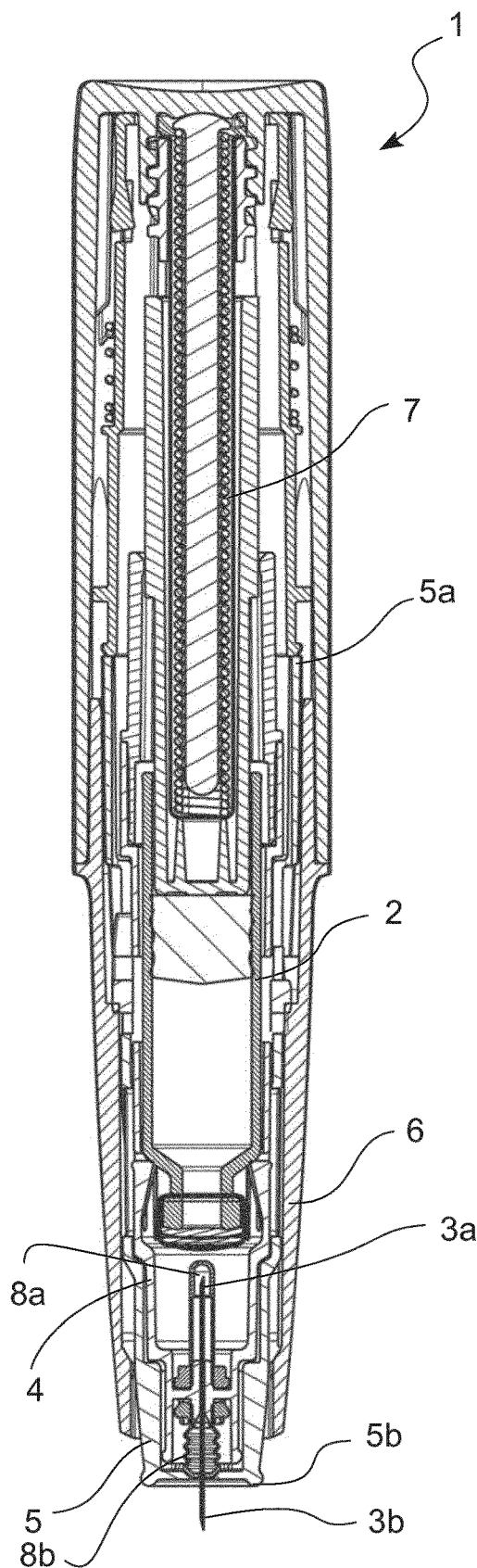
Fig. 1
Fig. 2

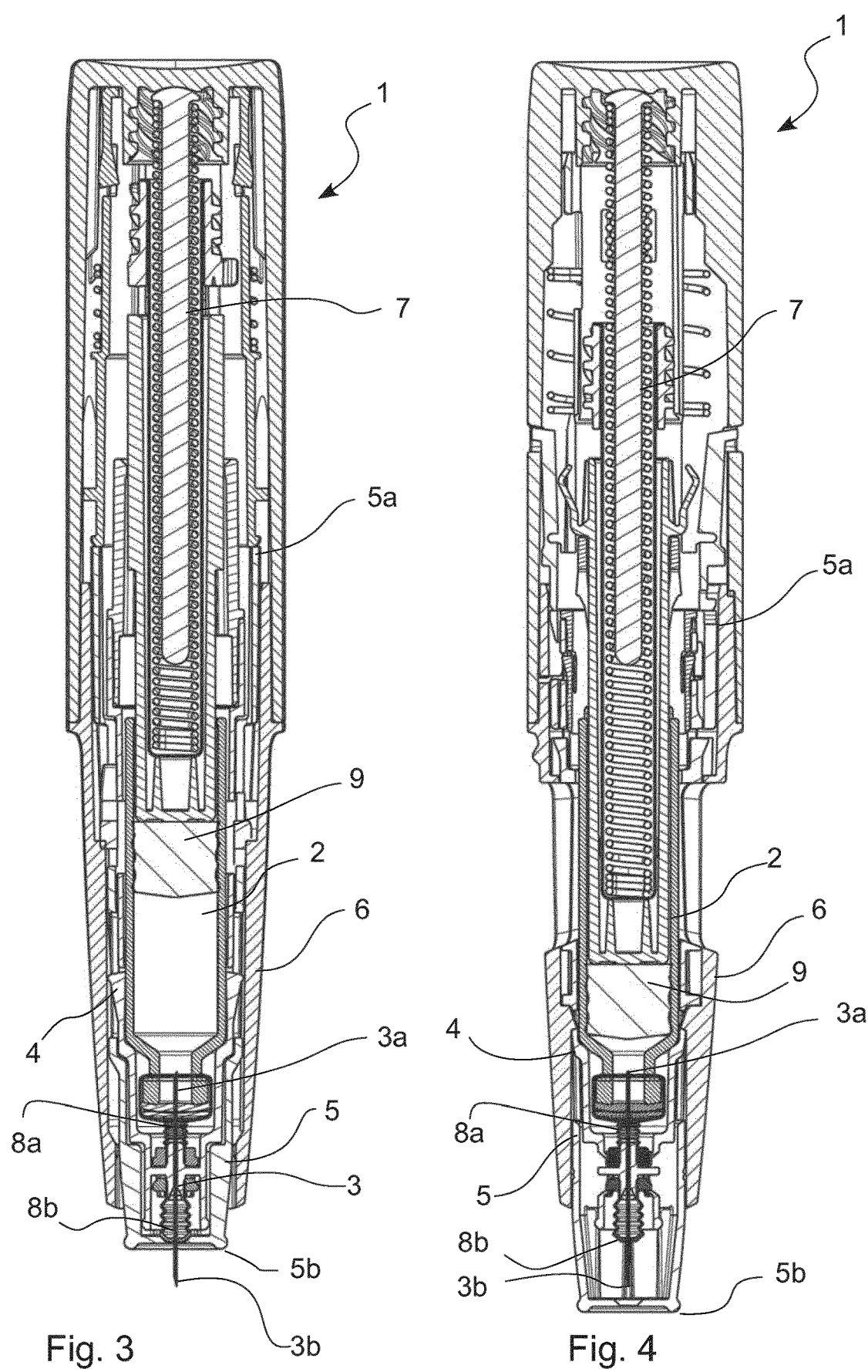

NEEDLE UNIT WITH A LOCKABLE NEEDLE SHIELD AND AN INJECTION DEVICE COMPRISING SUCH A NEEDLE UNIT

CROSS-REFERENCE TO RELATED APPLICATIONS

This application is a 35 U.S.C. § 371 National Stage application of International Application PCT/EP2016/050302 (published as WO 2016/110580), filed Jan. 8, 2016, which claims priority to European Patent Application 15150509.6, filed Jan. 8, 2015, the contents thereof which are incorporated by reference in their entirety.

FIELD OF THE INVENTION

The present invention relates to a needle unit with a lockable needle shield and an injection device for injecting a medicament comprising such a needle unit.

As used herein, the term "medicament" is meant to encompass any flowable drug capable of being passed through a delivery means such as a hollow needle or cannula in a controlled manner. Examples of flowable drugs are a liquid, a solution, a gel or a fine suspension. Also lyophilized drugs which prior to administration are dissolved into a liquid form are encompassed by the above definition. Representative medicaments includes for example pharmaceuticals, peptides, proteins (e.g. insulin, insulin analogues and C-peptide), hormones, biologically derived or active agents, hormonal and gene based agents, nutritional formulas and other substances in both solid (dispensed) or liquid form.

BACKGROUND OF THE INVENTION

In relation to some diseases patients must inject a medicament on a regular basis such as once weekly, once daily or even a plurality of times each day. In order to help patients overcome fear of needles, fully automatic injection devices have been developed with the aim of making the use of the injection device as simple and safe as possible. Such devices are typically designed such that a user shall position the injection device onto the injection site and activate the device. Such activation causes the device to insert a needle into the skin, eject a dose of the medicament and subsequently move the needle into a shielded position.

Prior to the actual use of the device by an end user, the needle must be assembled with the injection device. It is desired that the user does not need to handle the needle at all which requires pre-mounting of the needle with the injection device. Prior to mounting the needle on the injection device, a number of additional process steps are typically required, for example sterilization of the needle itself. It is therefore desired to provide a needle unit which is easy to handle prior to being mounted on the injection device without risking injury to people handling the needle unit and without risking damage to the needle.

In some injection devices, the needle is protected by a penetrable cover element, for example a silicone foil like cover element, which maintains a sterile barrier around the needle itself. This flexible cover element is typically not so strong and can be easily damaged. It is therefore desired to protect the flexible cover element during handling to avoid damage to the cover which could destroy the sterile barrier effect of the cover.

A needle shield is therefore often arranged to encase the needle and any cover elements which ensure the sterility of the needle. The needle shield is often assembled together with the needle to form a needle unit. During handling of the needle unit, the shield element is locked in position with respect to the needle. When the needle is to be mounted on the injection device, the shield element needs to be removed from the needle or the needle shield needs to be unlocked so that the needle shield can be displaced with respect to the needle so as to expose the needle. One example of such a prior art device is disclosed in WO 08/077706. However, this needle unit is a complex unit comprising a number of elements including a spring. The needle unit is intended for insertion into a rigid and sterile container for maintaining sterility during storing and handling. Typically such containers are sealed off by a planar seal that needs to be manually peeled off prior to mounting of the needle unit on an injection device. Such needle unit is not easily incorporated into an injection device at the time of manufacture.

Having regard to the above-identified prior art devices, it is an object of the present invention to provide a needle unit and an injection device comprising a needle unit that are improved with regards to locking of the needle shield prior to mounting of the needle unit on the injection device and unlocking of the needle shield during/after mounting of the needle unit on the injection device.

Yet additional further objects of the invention are to provide measures for obtaining needle units and injection devices having a superior performance and, at the same time, enabling manufacture at a reduced cost.

BRIEF DESCRIPTION OF THE INVENTION

A first aspect the present invention relates to a needle unit for cooperation with an injection device comprising a housing and a lock release element, the needle unit comprising:
  a needle hub comprising a needle having a proximal end, a distal end and a longitudinal axis extending between the proximal and distal ends, and
  a needle shield having a proximal end and a distal end,
  wherein the needle hub and the needle shield are arranged to form a needle unit where the needle hub is arranged displaceably inside the needle shield such that the needle hub is displaceable along an axis which is parallel with the longitudinal axis of the needle between a shielded position where the distal end of the needle shield extends distally past the distal end of the needle and where the proximal end of the needle shield extends proximally past the proximal end of the needle and an exposed position where the distal end of the needle extends distally past the distal end of the needle shield,
  characterized in that
  the needle hub further comprises a first hub locking element and a second hub locking element and in that the needle shield further comprises a first shield locking element and a second shield locking element,
  said first hub locking element and said first shield locking element engaging each other in the shielded position to establish a first releasable locking mechanism between the needle hub and the needle shield which when locked prevents the distal end of the needle from displacing in a distal direction with respect to the needle shield,
  said second hub locking element and said second shield locking element engaging each other in the shielded position to establish a second locking mechanism between the needle hub and the needle shield to prevent the proximal end of the needle from displacing in a proximal direction with respect to the needle shield, both the first and second locking mechanisms being arranged as shock proof locks, and wherein the first releasable lock mechanism is arranged to engage with the lock release element of the injection device when the needle unit is coupled to the injection device, said engagement allowing the first releasable lock mechanism to be unlocked.

According to the current specification, the terms distal and proximal are used to describe the placement of the different elements with respect to each other. The term distal end should be understood as being the end which is closest to the skin of the user during injection while the term proximal end should be understood as the end which is farthest from the skin of the user during injection. In general, the user will hold the proximal end of the device while placing the distal end of the device on the skin during injection.

The term "displacement in a distal direction" refers to motion which is arranged in a direction which is defined by a vector pointing from the proximal end to the distal end of the device. Likewise the term "displacement in a proximal direction" refers to motion which is arranged in a direction which is defined by a vector pointing from the distal end to the proximal end of the device.

Furthermore, the term "shock proof lock" should be understood as a locking mechanism which cannot be accidentally opened by subjecting the locking mechanism to a shock load. For example a friction press fit lock would not be a shock proof locking mechanism since a shock in the right direction could cause the elements to disengage with each other.

In some embodiments, the needle unit further comprises a pierceable distal cover element forming a sterility seal that seals off the needle at portions distal to the needle hub. Alternatively, or in addition, the needle unit may further comprise a pierceable proximal cover element forming a sterility seal that seals off the needle at portions proximal to the needle hub. The cover elements may be made of a material that enables damp sterilisation of the entire needle unit in its assembled state, such as damp sterilisation.

Each of the distal cover element and the proximal cover element may be configured as a collapsible penetrable boot that, when an axially compression force acts on the cover element, collapses axially causing the needle to pierce and penetrate the cover element.

The needle unit may be so formed that, when a plurality of similar needle units are arranged in bulk, no part of a needle unit will be able to contact the proximal cover element of other of the needle units arranged in bulk, irrespective of their relative orientation. Likewise, the needle unit may be formed so that when a plurality of like needle units are arranged in bulk, no part of a needle unit will be able to contact the distal cover element of other of the needle units arranged in bulk, irrespective of their relative orientation.

In one embodiment, the needle hub and the needle shield are manufactured as injection moulded components and the first hub locking element and the first shield locking element are integrated elements of the injection moulded components. Likewise, the second hub and second shield locking elements could also be integrated into the injection moulded components.

In one embodiment, the first releasable locking mechanism and the second locking mechanism are arranged as two independent locking mechanisms. In this way, the action of the two locking mechanisms can be separated into two separate functions. However, in another embodiment, the first releasable locking mechanism and the second locking mechanism could be integrated into a single mechanism. For example, instead of an arm with a free end which engages with a end surface of a slot as shown in the current embodiments, the end of the flexible arm could be formed as a hook which engages with a corresponding groove in the side of a slot in the shield element to prevent motion of the needle hub both in a distal and in a proximal direction with respect to the shield element.

In another embodiment, the needle hub and the needle shield are prevented from rotating with respect to each other around the longitudinal axis of the needle. In this way, respective motion of the needle shield and the needle hub along the longitudinal axis of the needle can be used to force elements of the needle shield/needle hub to displace sideways without simultaneous rotation of the two elements.

In one embodiment, the first releasable locking mechanism and/or the second locking mechanism are arranged proximally to the proximal end of the needle. In this way, the front end of the device where the needle is placed can be made simpler while the locking mechanisms are placed behind the needle where there is more room.

The needle shield may be arranged coaxially with the needle hub. In some embodiments the needle shield surrounds all parts of the needle hub. In other embodiments the needle hub may comprise elements located radially inwards relative to the needle shield while having other elements that extend radially exterior to the needle shield.

Subsequent to becoming unlocked, the first releasable lock mechanism assumes a state wherein the needle unit is in an unlocked state. In the unlocked state, movement of the needle hub is enabled for displacement in the distal direction relative to the needle shield. Prior to the needle unit is unlocked, the needle unit defines a locked state wherein no or only non-substantial relative axial displacement is possible between the needle shield and the needle hub.

In the context of a first embodiment, non-substantial relative axial displacement is defined as axial displacement which does not allow the cover elements to become penetrated by contact pressure of other needle units when like needle units are handled in bulk.

In the locked state of the needle unit, each of the cover elements, when present, may define a non-penetrated state wherein sterility of the needle is ensured.

When the needle unit assumes its locked state, engaging surfaces between first hub locking element and the first shield locking element prevents the needle hub from moving in a distal direction relative to the needle shield. At least one displaced element or displaced portion of an element of the first hub locking element and/or the first shield locking element is configured to be moved when engaged with the lock release element of the injection device when the needle unit is coupled to the injection device. When said displaced element or displaced portion of an element is moved to become unlocked, the movement may occur in an unlocking direction.

Engaging surfaces between first hub locking element and the first shield locking element may be so formed that, upon an increase in a force exerted for displacing the needle shield proximally relative to the needle hub, the displaced element will be increasingly urged in a direction opposite the unlocking direction.

In one embodiment, the first releasable locking mechanism is unlocked via the outer side of the needle shield. The phrase "via the outer side" should be understood in the current specification as requiring an action which is performed on the outer side of the shield element. In the prior art, the locking mechanism is unlocked from the inside of the needle unit. By arranging the locking mechanism such that it can be opened from the outside of the needle shield, a more flexible unlocking procedure can be provided.

In one embodiment, this can be provided by providing an opening in the side of the needle shield through which the first locking mechanism is unlockable. The opening may be provided as a hole or as an elongated slot. In another embodiment, one could imagine a flexible portion of the needle shield which could be depressed from outside the needle shield to cause the first releasable locking mechanism to unlock. It should be noted that providing a needle unit which is unlockable from outside the needle shield could be the subject of a divisional application without requiring the presence of a displaceable shield element which extends past both the distal and proximal ends of the needle as currently defined in the claims.

In one advantageous embodiment the first releasable locking mechanism is arranged to automatically unlock when the needle unit is coupled to the housing of the injection device. In this way, the unlocking is arranged without any complicated actions being required during assembly of the injection device.

A second aspect of the invention relates to an injection device comprising a needle unit as described above, a housing and a lock release element, where the lock release element of the injection device is arranged as a fixed portion of the housing of the injection device and the first locking mechanism is arranged to automatically unlock when the needle unit is coupled to the housing.

In some embodiments where the first releasable locking mechanism is automatically unlocked by the needle unit being coupled to the housing of the injection device the rear cover maintains its non-penetrated state even as the coupling between the housing and the needle unit is carried out.

In one embodiment, the injection device further comprises a container comprising a medicament and an expelling assembly.

In one embodiment the lock release element is a ramp element and the first hub locking element and/or the first shield locking element are arranged to be displaced by the ramp element to unlock the first locking mechanism when the needle unit is coupled to the injection device. It should be noted that in the embodiment shown in the figures, the first hub locking element is arranged to be displaced to unlock the first releasable locking mechanism. However, in another embodiment, the first shield locking element could be arranged to be displaced to unlock the first releasable locking mechanism.

In some embodiments, one or both cooperating surfaces of the ramp element and the first hub locking element and/or the first shield locking element comprise surface elements that are inclined with respect to the longitudinal axis so as to impart a sideways force on the displaced element as the needle unit is displaced during coupling to the housing of the injection device. When acted on by the ramp element of the housing, a free end of the displaced element moves in an unlocking direction.

The first hub locking element and the first shield locking element may include engaging surface elements having a normal that is inclined with respect to the longitudinal axis, such as forming an angle less than 25 degrees relative to the longitudinal axis. Said engaging surface elements may be formed so that, when the needle unit assumes its locked state, upon an increase in force exerted for displacing the needle shield proximally relative to the needle hub, a free end of the displaced element will be increasingly urged in a direction opposite the unlocking direction.

In one embodiment, the first hub locking element or the first shield locking element is a flexible arm which is bendable about an axis which is perpendicular to the longitudinal axis of the needle and/or perpendicular to the outer surface of the needle hub and the lock release element is a ramp element with a ramp surface arranged on the inner surface of the housing and arranged to form an angle to the longitudinal axis of the needle of between 10 and 65 degrees, preferably between 10 and 45 degrees and even more preferably between 10 and 35 degrees.

In another type of embodiment, the lock release element is connected to a displaceable element on the outer surface of the housing, said displaceable element being displaceable by a user of the injection device and where the first locking mechanism is arranged such that displacement of the displaceable element displaces the lock release element which releases the first releasable lock mechanism. In this way, an unlocking action needs to be manually performed by the user before the needle can be exposed. This provides an extra layer of security. For such embodiment, where a rear cover is present, the rear cover maintains its non-penetrated state even subsequent to releasing of the first releasable lock mechanism.

A third aspect of the invention relates to a method of manufacturing an injection device, the manufactured injection device comprising a needle shield having a proximal end and a distal end, a needle hub and a housing, said needle hub comprising a needle having a distal end, a proximal end and a longitudinal axis extending from the distal end to the proximal end, the needle hub and the needle shield being movable axially relative to each other for shifting the needle from a shielded state to an exposed state, said needle shield being arranged such that in the shielded state, the proximal end of the needle shield extends proximally past the proximal end of the needle and the distal end of the needle shield extends distally past the distal end of the needle and that in the exposed state the distal end of the needle extends distally past the distal end of the needle shield, the method comprising the steps of:

a) providing a needle hub, the needle hub comprising a first hub locking element, b) providing a needle shield, the needle shield comprising a first shield locking element configured to cooperate with the first hub locking element, c) securing the needle hub and the needle shield relative to each other to form a needle unit wherein the needle is in the shielded state, d) moving the first hub locking element and the first shield locking element relative to each other to establish a first releasable locking mechanism between the needle hub and the needle shield which prevents the needle from being shifted into the exposed state by displacement of the needle relative to the needle shield in a direction defined by a vector pointing from the proximal end of the needle towards the distal end of the needle, the first releasable locking mechanism being arranged as a shock-proof lock, e) providing a housing, and f) assembling the needle unit with the housing and moving the first hub locking element and the first shield locking element relative to each other to release the first releasable locking mechanism for enabling axial movement between the needle shield and the needle hub to allow the needle to be exposed.

In another embodiment, the method further comprises the step of moving a second hub locking element of the needle hub relative to a second shield locking element of the needle shield to establish a second locking mechanism between the needle hub and the needle shield to prevent the needle hub from displacing relative to the needle shield in a proximal direction with respect to the needle shield.

In one embodiment, the step f) of assembling the needle unit with the housing comprises the step of releasing the first releasable locking mechanism by positioning the needle unit relative to the housing section whereby a release geometry or lock release element on the housing releases the first releasable locking mechanism.

In one further embodiment the method further comprises the steps of:
- g) providing a needle shield release button, the needle shield release button comprising a release geometry configured to operate and release the first releasable locking mechanism, and
- h) assembling the needle shield release button with the housing section and the needle unit.

In another embodiment, the first releasable locking mechanism is so configured that release of the first releasable locking mechanism requires relative movement of at least one of the first hub locking element and the first shield locking element in a direction which is not parallel with the longitudinal axis of the needle. In some embodiments, said relative movement of at least one of the first hub locking element and the first shield locking element is configured for movement in a direction which is substantially perpendicular to the longitudinal axis of the needle, such as movement in a tangential direction around the longitudinal axis.

In a further embodiment of the method, the method further comprises the step, subsequent to step d), of sterilizing the needle unit. In this way, the needle shield fully protects the needle during the sterilizing procedure and the subsequent handling and assembling of the needle unit.

It should be emphasized that the term "comprises/comprising/comprised of" when used in this specification is taken to specify the presence of stated features, integers, steps or components but does not preclude the presence or addition of one or more other features, integers, steps, components or groups thereof.

BRIEF DESCRIPTION OF THE DRAWINGS

In the following, the invention will be described in greater detail with reference to embodiments shown by the enclosed figures. It should be emphasized that the embodiments shown are used for example purposes only and should not be used to limit the scope of the invention.

FIG. 1 shows a sectional side view of one example of an injection device which is suitable for use with the current invention, the needle being in an initial shielded state.

FIG. 2 shows a sectional side view of the injection device of FIG. 1 in a state where the distal end of the needle fully protrudes from a needle shield.

FIG. 3 shows a sectional side view of the injection device of FIG. 1 in a state where a cartridge has been connected to the proximal end of the needle for fluid delivery and wherein expelling has been initiated.

FIG. 4 shows a sectional side view of the injection device of FIG. 1 in a state where the needle shield has returned to its original position to put the needle into a shielded state again.

DETAILED DESCRIPTION OF THE EMBODIMENTS

Figure 5:
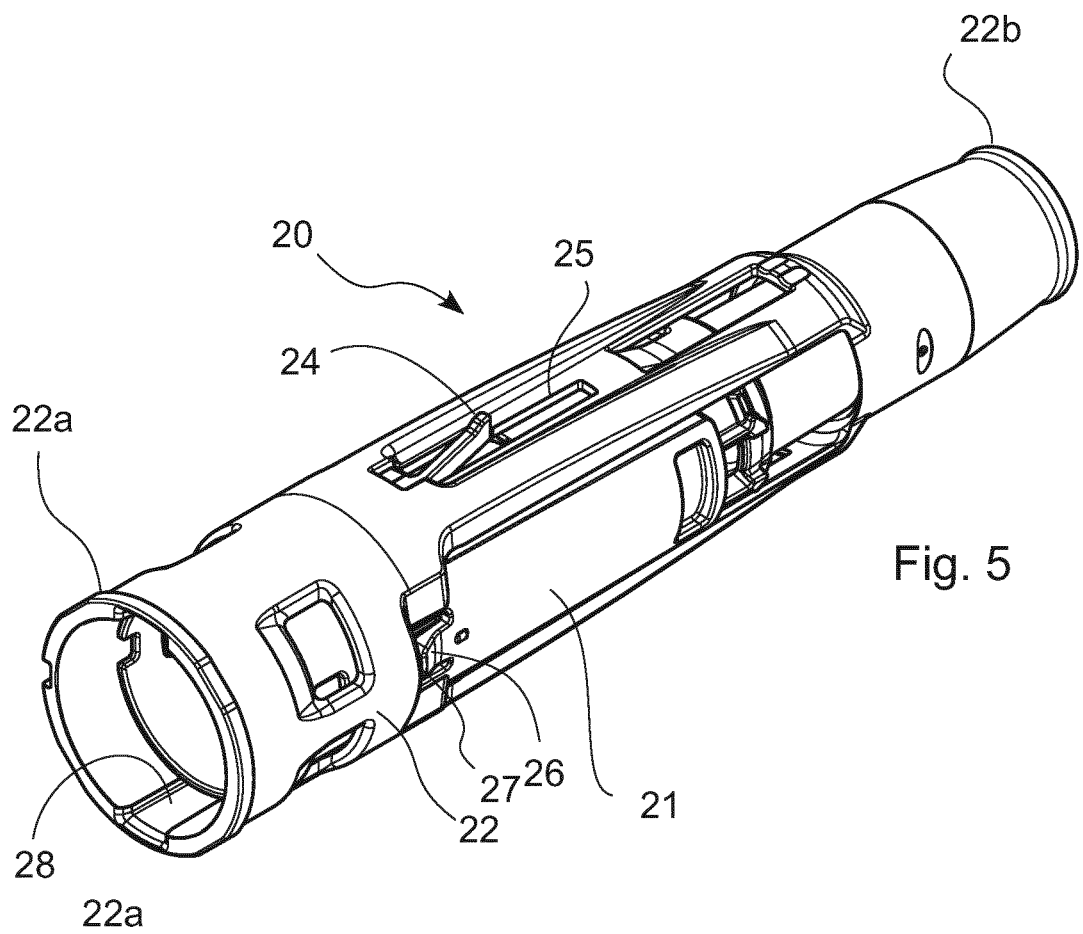
FIG. 5 shows a first perspective view of a first embodiment of a needle unit according to the current invention where the needle is in a locked and shielded state.
Figure 6:
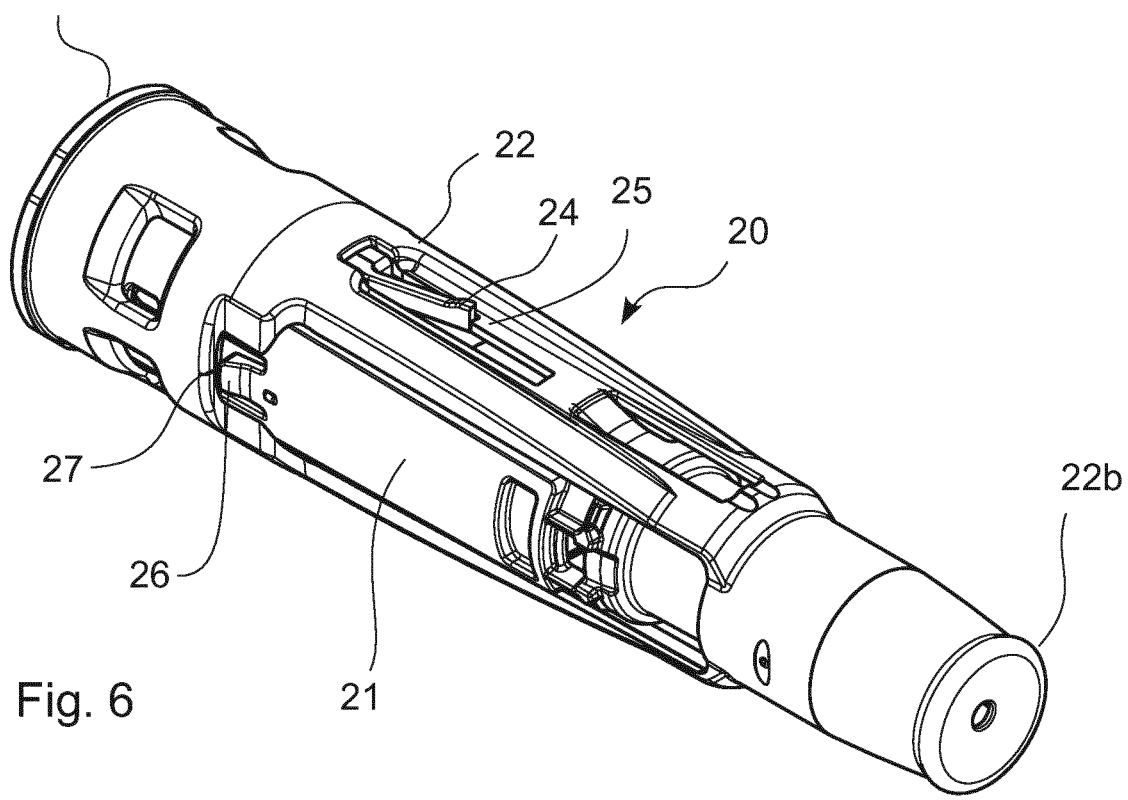
FIG. 6 shows a second perspective view of the needle unit of FIG. 5 in the same locked and shielded state.

FIGS. 1-4 show an example of an injection device in four different states of operation in order to explain the basic function of the device. The needle unit of the current invention can be used together with such an injection device, however the needle unit of the current invention can also be used with other forms of injection device. All the details of the injection device will not be described in detail since these details have already been described in other patent specifications of the current applicant, i.e. in WO 2015/150578, WO 2015/197866 and WO 2015/197867. Reference is made to these other specifications for additional details.

FIGS. 1-4 show an injection device 1 with a medicament containing cartridge 2, a needle 3 having a proximal end 3a and a distal end 3b, a needle hub 4, a needle shield 5 having a proximal end 5a and a distal end 5b, a housing 6 and an activation mechanism 7. The details of the activation mechanism will not be covered in this specification since the needle unit of the current invention will work with many different types of activation mechanisms.

In the current embodiment, in the shielded state as shown in FIG. 1, the proximal end 5*a* of the needle shield is arranged proximally to the proximal end 3*a* of the needle. Likewise, the distal end 5*b* of the needle shield is arranged distally to the distal end 3*b* of the needle. In this way, the needle is completely shielded by the needle shield. It can also be seen that in the current embodiment, the needle shield is a single element which encases the needle completely. When the needle shield is displaced with respect to the needle, both the distal and the proximal ends of the needle shield displace with respect to the needle. While this is also claimed in the current claims, in another embodiment which could be the subject of a divisional application, the needle shield could be arranged as a two component element whereby only the distal end of the needle shield would displace with respect to the needle shield, while the proximal end of the needle shield remains fixed in place relative to the needle.

As can be seen from FIG. 1, the needle 3 is arranged as a needle tube having two pointed ends, one arranged at the proximal end of the needle tube and one arranged at the distal end. The needle hub 4 grips the middle portion of the needle tube so that both the distal and the proximal ends of the needle are free. During use, the proximal end of the needle is arranged to engage with a container 2 containing the medicament which is to be injected while the distal end is arranged to pierce the skin of the user to inject the medicament into the body of the user. It should however be noted that the current invention could also be used in an embodiment of an injection device where the needle unit is arranged with only one pointed end and is connected to a source of medicament in another manner, without the use of a pierceable container as is shown in the current figures.

As can also be seen from FIG. 1, the proximal end 3*a* of the needle is covered by a proximal cover element 8*a* forming a sterility sheath made from a thin flexible penetrable material, such as a foil like silicon cover element. The distal end of the needle is also covered by a distal cover element 8*b* forming a sterility sheath also made from a thin flexible penetrable material, such as a foil like silicon cover element. The cover elements are arranged to allow the needle to be sterilized, such as by steam sterilization, and then ensure that the needle itself is not contaminated by further handling of the needle unit. Upon use of the injection device for drug administration, the distal and proximal pointed needle ends are configured to pierce and penetrate the respective cover element. In the embodiment shown, each of the distal and proximal cover elements are formed as generally cylindrical sheaths or boots that encircle and encapsulate the needle from the needle hub to the pointed needle end. The sterility sheaths in their non-penetrated state serve to maintain the needle in the sterile state right until use of the injection device.

In FIG. 2, the needle shield 5 has been retracted with respect to the needle hub such that the distal end 3*b* of the needle now extends distally past the distal end 5*b* of the needle shield. In this way the distal end of the needle is now exposed and ready for injecting medicament into a user. As can also be seen in FIG. 2, the act of retracting the needle shield has caused the distal cover element 8*b* to be pulled back. This causes the distal end of the needle to pierce through the cover element thereby uncovering the distal end of the needle. Due to the flexible nature of the cover element, the cover element is easily retracted.

In FIG. 3, it can be seen that the activation mechanism has pushed the medicament containing cartridge 2 forward in a distal direction to engage the cartridge with the proximal end of the needle. The proximal end of the needle punctures the lid/septum of the cartridge thereby establishing a fluid path from the cartridge through the needle and to the distal end of the needle whereby the medicament can be injected into the user. As can also be seen in FIG. 3, the proximal cover element 8*a* has also been compressed by the motion of the cartridge towards the needle. This causes the proximal end 3*a* of the needle to pierce and penetrate through the proximal cover element 8*a* thereby uncovering the proximal end of the needle allowing it to engage with the cartridge.

In FIG. 4, the activation mechanism has pushed a piston 9 arranged in the cartridge downwards, thereby causing the medicament in the cartridge to be injected through the needle into the user. After the medicament has been injected, the needle shield is again pushed forward with respect to the needle hub to shield the distal end of the needle.

The description above with respect to FIGS. 1 to 4 has been provided to give a background of the use of an injection device. The injection device described is one of many different available injection devices. It should be noted that the needle unit of the current invention can be used with different injection devices, not just the one described above with respect to FIGS. 1 to 4. It should also be noted that the specific locking elements discussed in the description below are not disclosed in FIGS. 1-4, however, it will be clear that the needle shield and needle hub shown in FIGS. 1-4 could be easily modified to comprise the locking elements and locking functions of the embodiments described below.

FIGS. 5 to 13 show different views of a first embodiment of a needle unit 20 according to the current invention and its components. The needle unit comprises a needle hub 21, a needle 23 and a needle shield 22. The needle hub grips the needle so that these components are fixedly attached to each other thus forming an injection needle assembly, see FIGS. 12 and 13. The needle 23 is formed as a needle tube with a proximal pointy end 23*a* and a distal pointy end 23*b*. Other embodiments may include a needle that is made by two cannula parts that are joined for fluid communication.

As discussed with reference to FIGS. 1 to 4, the needle unit 20 may include cover elements forming penetrable sterility seals that seals off the proximal end 23*a* and the distal end 23*b* of the needle 23. Such cover elements will be further discussed in relation to the second embodiment of a needle unit shown in FIGS. 14 to 20. However, in FIGS. 5 to 13 such cover elements are either not visible or not shown.

In the current embodiment, both the needle shield and the needle hub are manufactured as injection moulded plastic components. Both elements are furthermore arranged as cylindrical and slightly tapered elements with a proximal end being wider than the distal end.

The needle hub is arranged to be inserted into the proximal end of the needle shield during assembly. The needle shield and the needle hub are furthermore arranged such that the needle hub can slide back and forth inside the needle shield in a direction which is parallel to the longitudinal axis of the needle hub and the needle shield.

However, as mentioned previously, it is desired to ensure that the needle shield does not displace accidentally to thereby accidentally penetrate the cover elements and/or expose the needle during handling of the unit. The needle unit of the current invention therefore has locking mechanisms to lock the position of the needle hub with respect to the needle shield. In the current embodiment, two separate locking mechanisms are provided, a first releasable locking mechanism for ensuring that the needle hub does not displace in a distal direction with respect to the needle shield and a second mechanism for ensuring that the needle hub does not displace in a proximal direction with respect to the needle shield.

The first locking mechanism is provided with a first hub locking element 24 fastened to the needle hub and a first shield locking element 25 fastened to the needle shield. In the current embodiment, the first hub locking element 24 is arranged as a flexible arm which is flexible about an axis which is perpendicular to the longitudinal axis of the needle hub and normal to the outer surface of the needle hub. The first shield locking element 25 is arranged as a stepped slot in the needle shield. When the needle hub is inserted into the needle shield, the free end of the flexible arm engages a first step of the stepped slot, thereby preventing further displacement of the needle hub distally with respect to the needle shield. However, the end of the flexible arm can be displaced by bending the arm to disengage the free end of the arm with the first step, i.e. in a direction which will be referenced "the unlocking direction", a direction which is counter to a direction which will be referenced "the locking direction". Once the locking mechanism has been unlocked, the needle hub can be displaced further distally with respect to the needle shield, thereby exposing the needle as shown by comparing FIGS. 12 and 13.

The second locking mechanism is provided with a ramped flexible flange 26 on the needle hub which is depressed slightly when inserting the needle hub into the needle shield. When the needle hub is inserted a certain distance into the needle shield, the ramped flange passes a cutout 27 in the needle shield and snaps outwardly, thereby preventing the needle hub from displacing in a proximal direction with respect to the needle shield.

It can be seen that both the first and the second locking mechanisms are arranged as shock proof arrangements since the motion required to unlock the mechanisms and the motion required to displace the needle hub with respect to the needle shield are in different directions. For example, in order to retract the needle hub out of the needle shield, it would be required to simultaneously depress the two ramped flanges 26 on either side of the needle hub while also pulling the needle hub in a proximal direction. This would be impossible in a shock situation.

In this respect it can also be noted that the needle shield comprises two first shield locking elements, one arranged on each side of the needle shield. The same is true for the first hub locking elements and the second hub and shield locking elements. In this way, it is doubly ensured that the locking mechanisms do not open accidentally.

Figure 7:
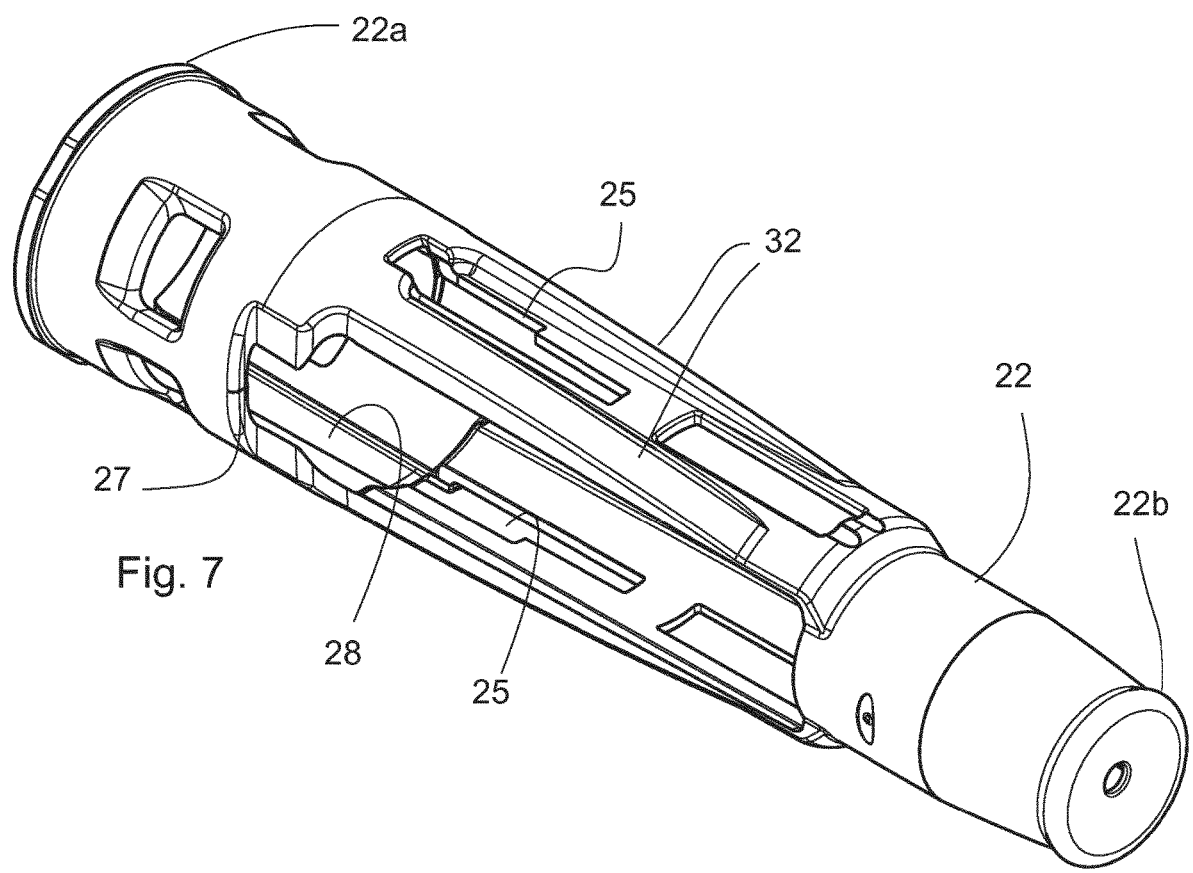
FIG. 7 shows a perspective view of the needle shield of the needle unit of FIG. 5.
Figure 8:
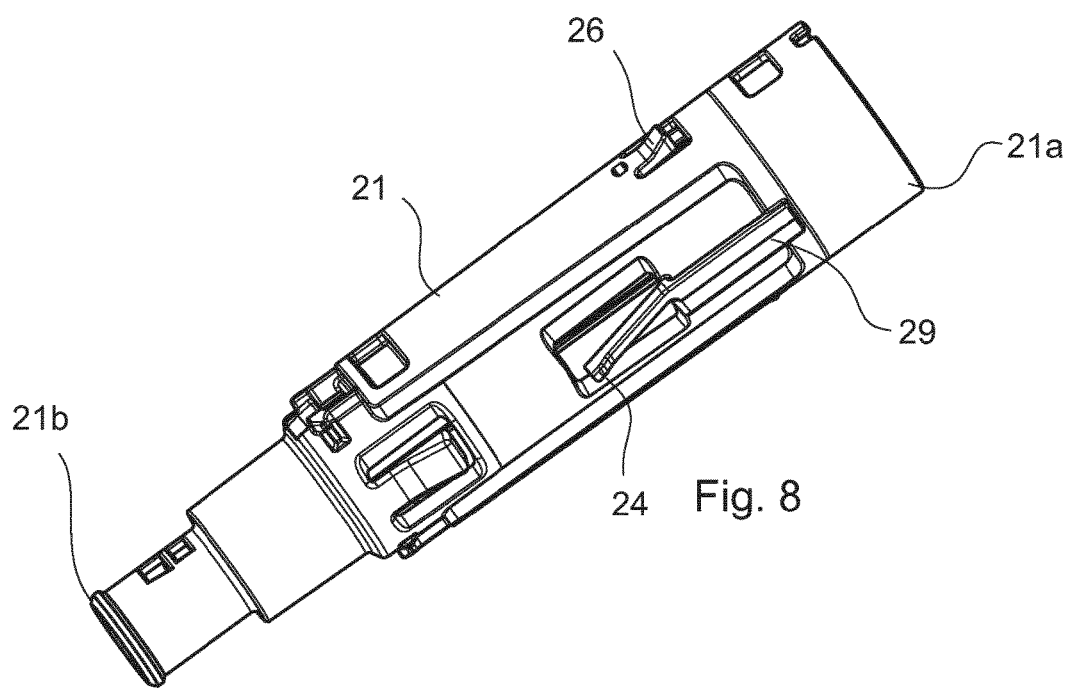
FIG. 8 shows a perspective view of the needle hub of the needle unit of FIG. 5, but without the needle.

Furthermore, it can be seen from FIGS. 7 and 8 that the needle shield is provided with a groove 28 arranged parallel to the longitudinal axis of the needle shield which engages with an elongated protrusion 29 on the needle hub. In this way, the needle hub is prevented from rotating with respect to the needle shield about the longitudinal axis of the needle shield. Again, it should be noted that a groove and an elongated protrusion is provided on both sides of the needle shield and needle hub respectively.

When the needle shield is assembled with the needle hub, it is desired that the needle shield cannot displace with respect to the needle hub during handling of the needle unit. Hence, the needle unit is in a locked state. In the shown embodiment, when the needle unit assumes the locked state, no or only little relative axial displacement between the needle shield and the needle hub is possible. In other embodiments, more relative axial displacement is possible, however to a degree where there is no risk that any of the cover elements becomes penetrated unintentionally.

However, once the needle unit is assembled with the injection device, it becomes necessary for the needle shield to be able to displace with respect to the needle hub so that the needle can become exposed when desired. It is therefore required to unlock the first locking mechanism. In the current embodiment, this is done automatically when the needle unit is inserted into the housing 30 of the injection device. As can be seen from FIGS. 9 to 11, the front portion of the housing 30 is also cylindrical with a slightly conical form where the proximal end is slightly larger than the distal end. The needle unit is inserted into the proximal end of the housing during assembly. A ramp element 31 provided on the inside surface of the housing 30 is arranged to automatically displace the free end of the flexible arm 24 of the needle hub sideways to disengage it with the stepped slot in the needle shield. In this way, the needle hub can then be displaced with respect to the needle shield. Ridges 32 on the needle shield engage with grooves 33 on either side of the ramp element 31 in order to prevent the needle shield from rotating with respect to the housing during insertion of the needle shield in the housing.

Figure 9:
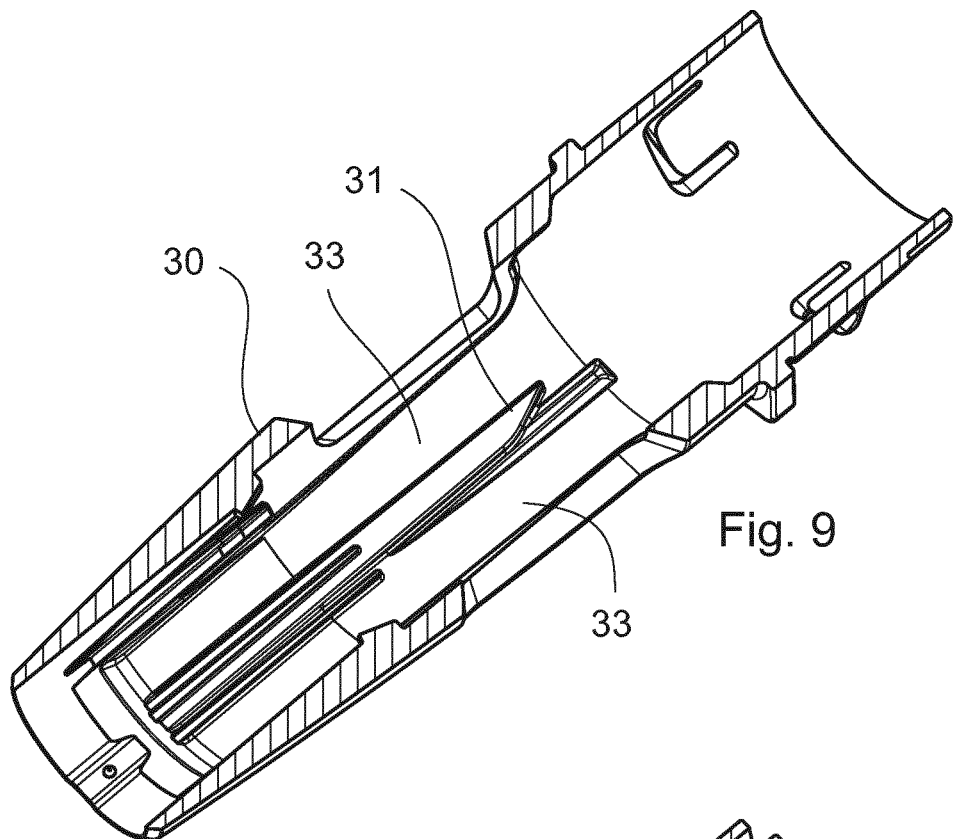
FIG. 9 shows a perspective partial section view of a housing of an injection device.
Figure 10:
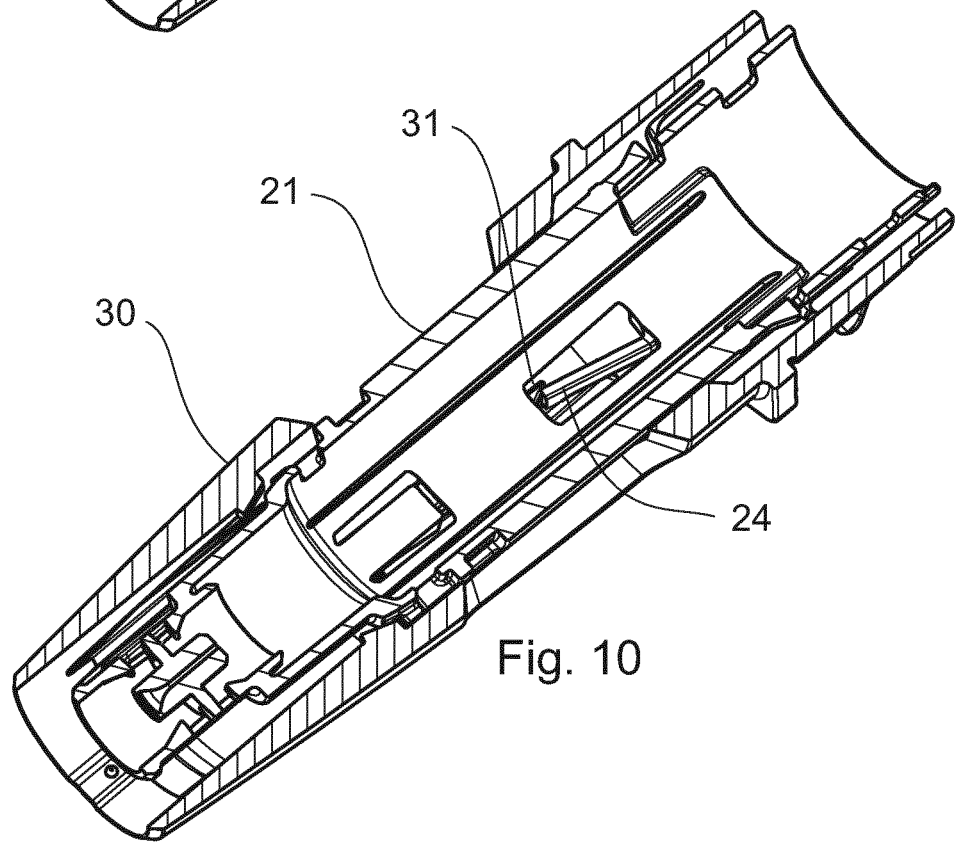
FIG. 10 shows a perspective partial section view of the needle hub of FIG. 8 inserted into the housing of FIG. 9 in a locked position, but without the needle shield or needle being shown.
Figure 11:
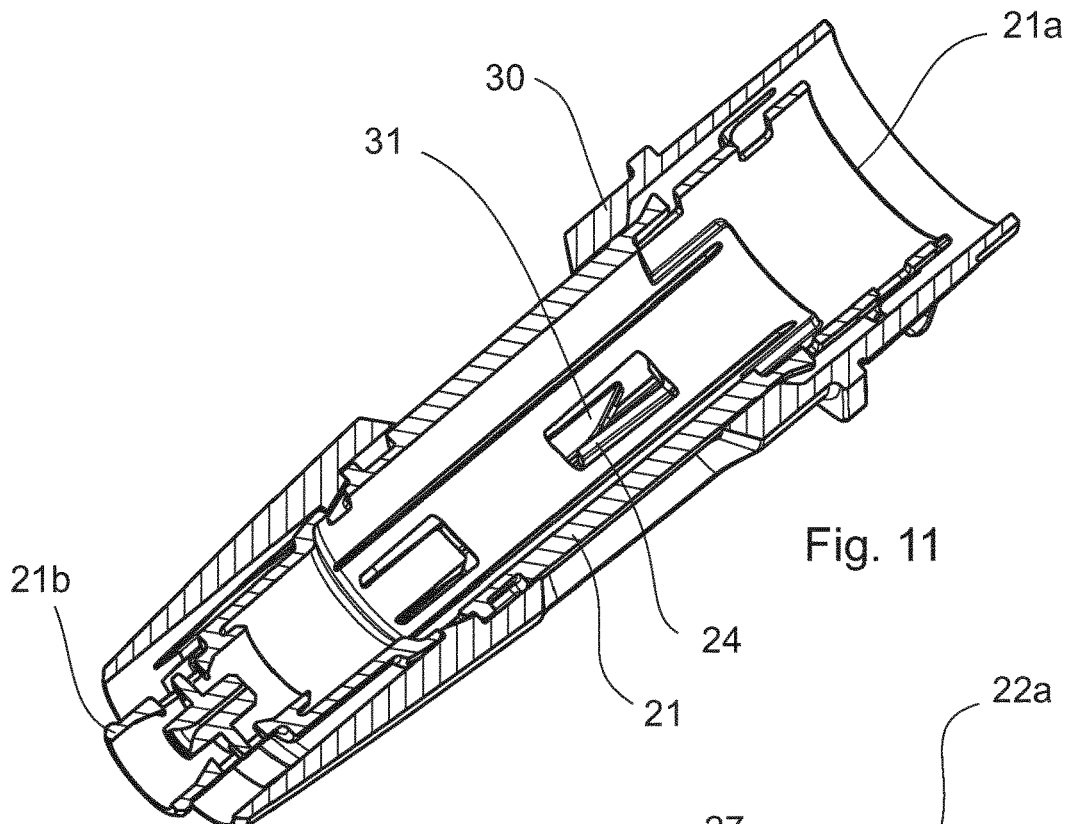
FIG. 11 shows a perspective partial section view of the needle hub of FIG. 8 inserted into the housing of FIG. 9 in an unlocked position, again without the needle shield or needle being shown.

FIG. 9 shows the housing 30 where the ramp element 31 and the grooves 33 can easily be seen. FIGS. 10 and 11 show how the needle hub without the shield element has been inserted into the housing. It should be noted that during insertion in the real assembly procedure, the assembled needle unit with both the needle shield and the needle hub will be inserted. However for the sake of illustration, FIGS. 10 and 11 show just the needle hub so that it is easier to see the interaction between the flexible arm 24 and the ramp element 31. In FIG. 10, one can see the free end of the flexible arm 24 just engaging the end of the ramp element 31. As the needle hub is pressed further into the housing, the ramp element causes the free end of the flexible arm to be pushed more to the side as shown in FIG. 11 where the arm has been completely displaced to the side.

Figure 12:
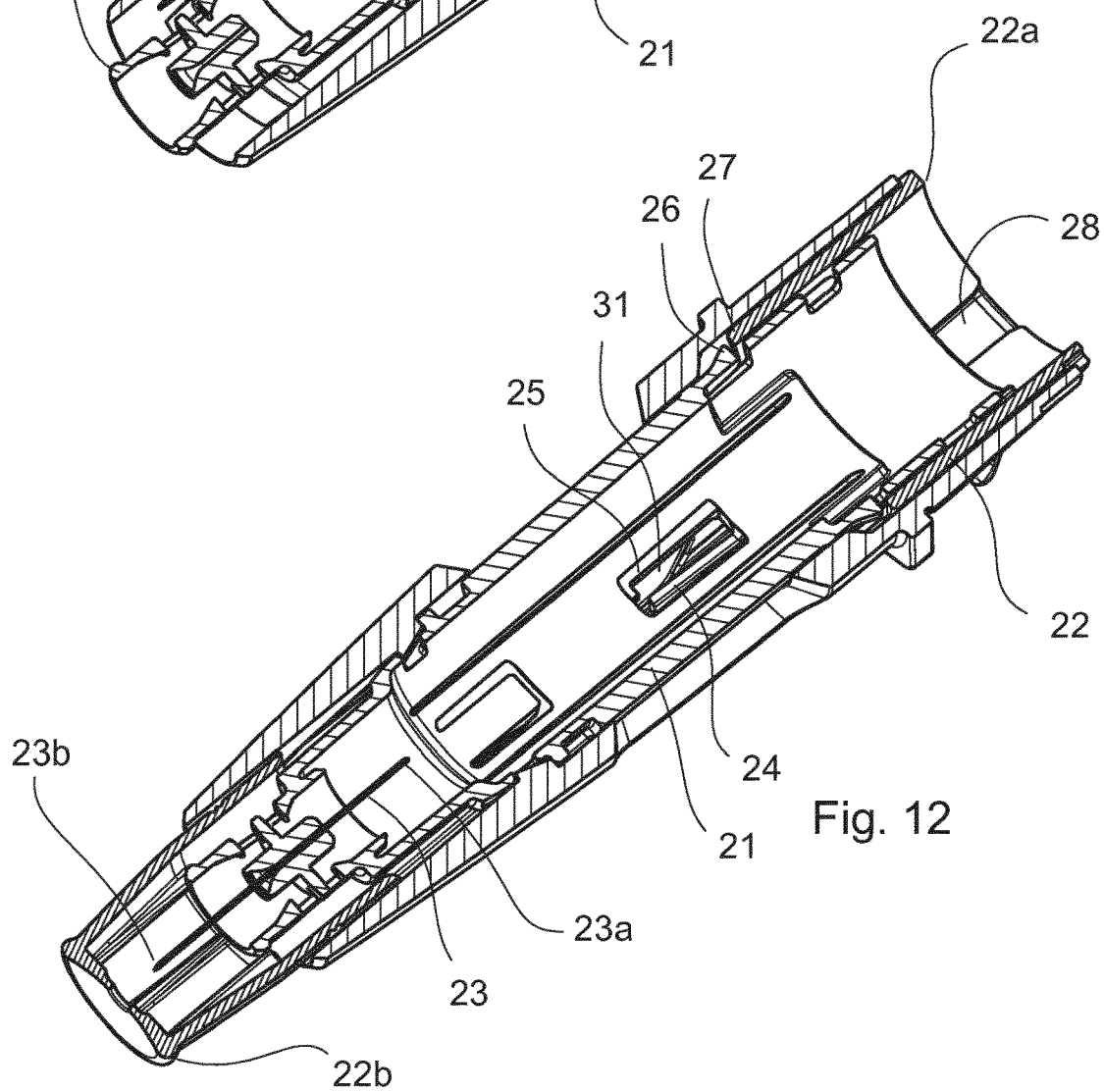
FIG. 12 shows a perspective partial section view of the view of FIG. 11, but with the needle shield and the needle also shown.
Figure 13:
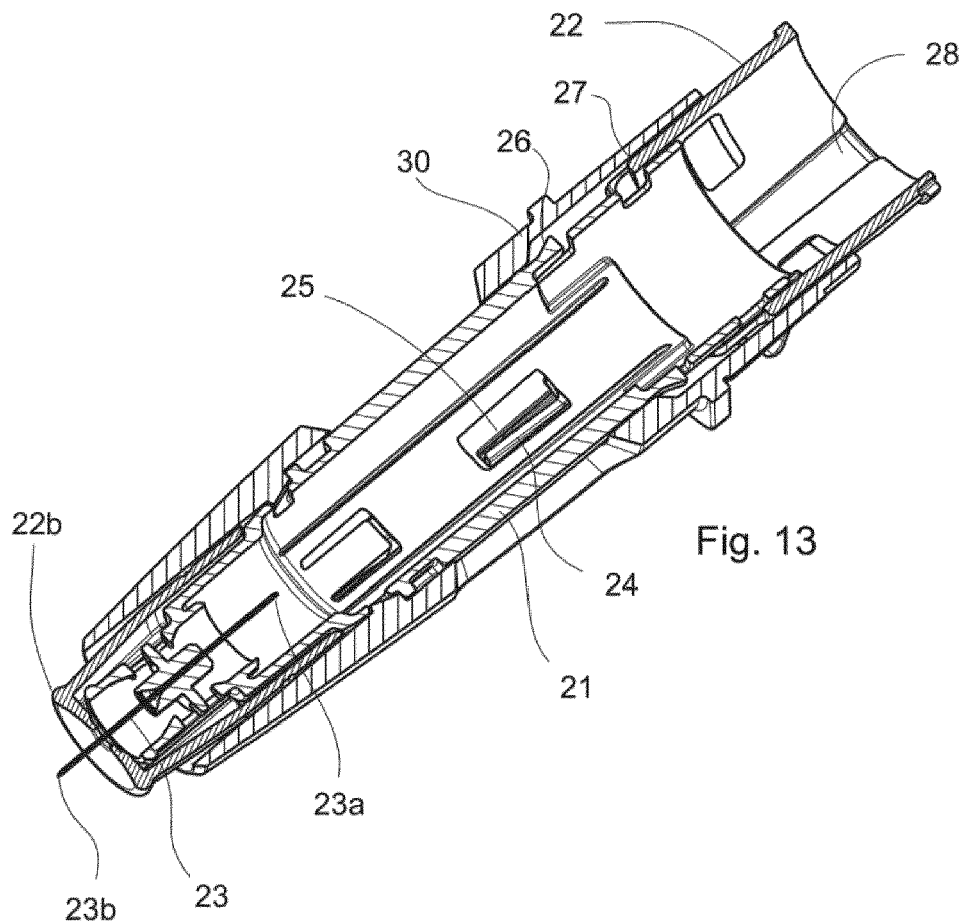
FIG. 13 shows a perspective partial section view of the view of FIG. 12, but with the needle shield retracted to expose the needle.

FIGS. 12 and 13 now include the needle shield and the needle 23. In FIG. 12 it can be seen that the free end of the arm 24 has been pushed so far to the side, that it is no longer engaged with the end of the first step of the stepped slot 25. As such the needle shield can now be displaced further towards the proximal end of the device. This is shown in FIG. 13 where the needle shield has been pushed towards the proximal end thereby exposing the distal end 23*b* of the needle 23. In this position, it can be seen that the free end of the flexible arm 24 has reached the bottom of the stepped slot and the needle shield cannot be displaced further in a proximal direction with respect to the needle hub.

It should be noted that there are additional mechanical elements on the body of the needle hub and the needle shield which interact with each other. However these details are not essential for the current invention and will therefore not be discussed further here. The interested reader is referred to other patent specifications of the current applicant which describe these features.

Figure 14:
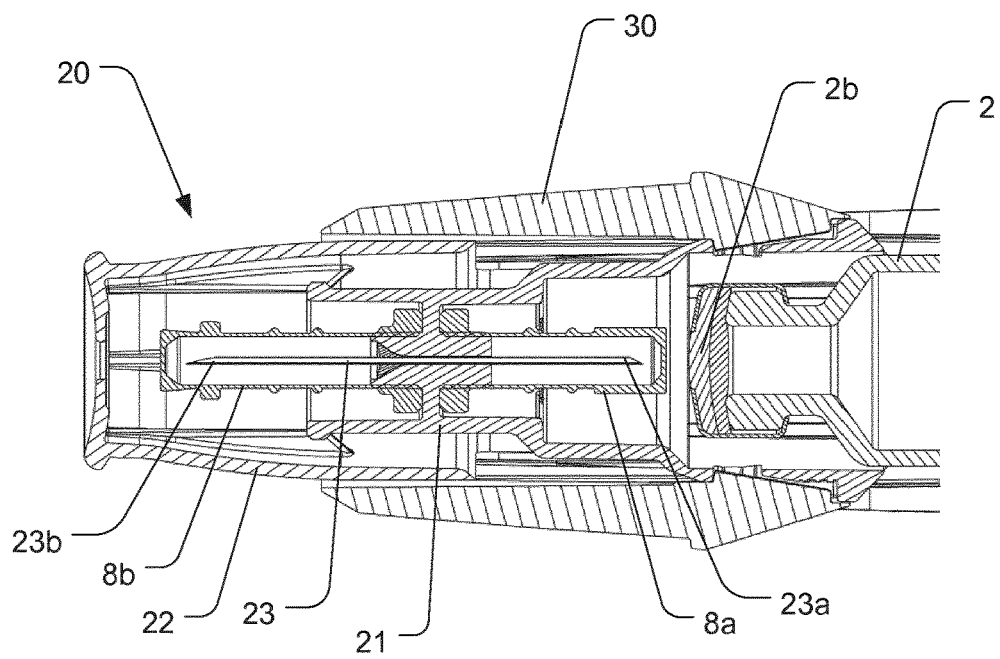
FIG. 14 shows a cross sectional view of a second embodiment of a needle unit according to the invention, the view showing the distal part of the needle unit in its shielded state and together with a container inserted into the housing.

FIG. 14 shows a cross sectional view of a second embodiment of a needle unit according to the invention. Relative to the previous views, FIG. 14 shows the needle unit 20 with two cover elements 8*a* and 8*b* attached to the hub 21 respectively covering the proximal end 23*a* and the distal end 23*b* of the needle cannula.

FIG. 14 shows the needle unit 20 after it has been assembled into the lower housing of housing 30 of the injection device and with a cartridge 2 being retained in a spaced apart configuration relative to the proximal end 23a of the needle. This state correspond to the storage state of the device. As discussed in WO 2015/197867, two resilient arms (referenced 530 in that disclosure) retain the cartridge and prevent the cartridge from being moved distally until point of use. Such resilient arms are also shown (non-referenced) in the appended drawings and thus serve to prevent the cartridge septum 2b and the rear cover element 8a from touching each other to prevent a potential premature penetration of these pierceable elements.

The second embodiment of the needle unit 20 has mainly been modified relative to the first embodiment for ensuring increased robustness of the locking function relating to elements 24, 25 and ramp element 31 and to provide a more robust design in view of tolerances.

Figure 15:
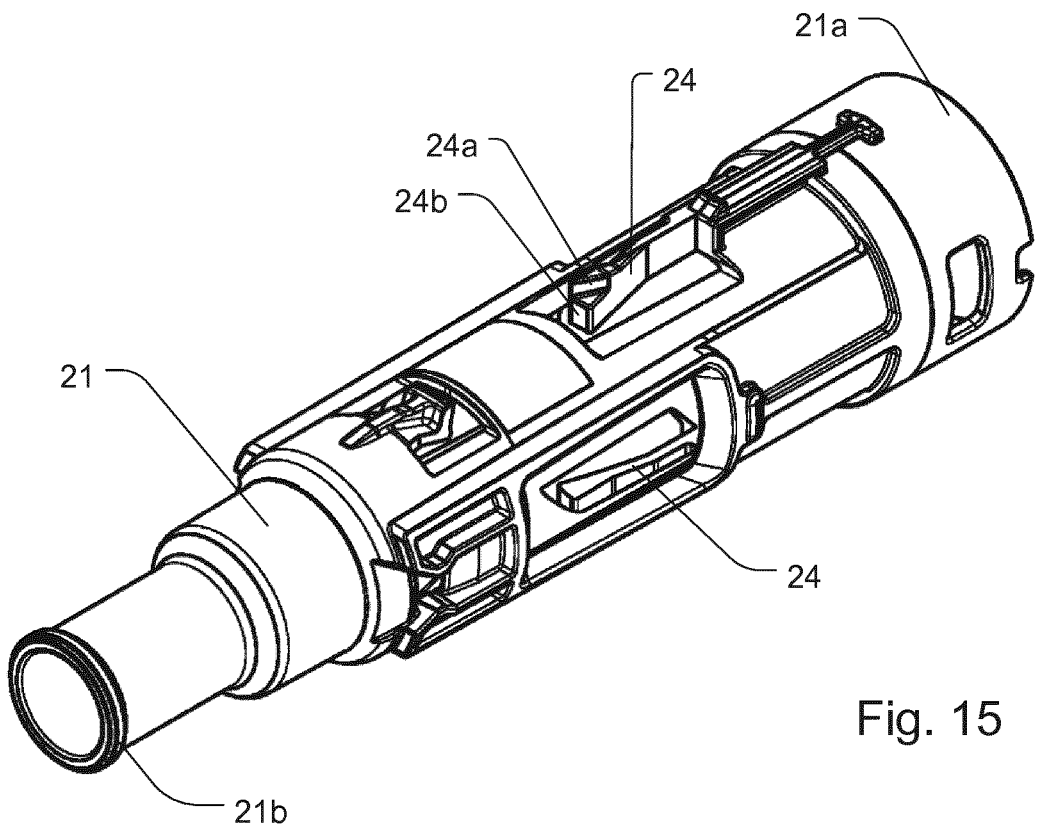
FIG. 15 shows a perspective view of the needle hub of the needle unit of FIG. 14, but without the needle.

FIG. 15 shows a perspective view of the needle hub of the needle unit 20 of the second embodiment, but without the needle and cover elements being shown. Again, a first hub locking element 24 is arranged as a flexible arm that extends generally parallel with the longitudinal axis. Flexible arm 24 is flexible about an axis which is perpendicular to the longitudinal axis of the needle hub and normal to the outer surface of the needle hub. Thus the distal free end of the flexible arm is able to bend sideways in a tangential direction. Flexible arm at its distal free end includes a first surface 24a that is configured for cooperation with the ramp element 31 of the housing 30. Further the flexible arm includes a second surface 24b that is configured for cooperation with the first shield locking element 25 of the needle shield 22. The second surface 24b of flexible arm exhibits a surface that substantially faces the distal direction, i.e. having a normal substantially parallel with the longitudinal axis. The design of the first shield locking element 25 of the needle shield 22 has generally been maintained unchanged relative to the first embodiment. The surface 24b and the cooperating surface arranged on the stepped slot 25, i.e. the first step of the stepped slot, have been formed so that, when the needle unit assumes its locked state, upon an increase in force exerted for displacing the needle shield 22 proximally relative to the needle hub 21, the flexible arm will be increasingly urged in the locking direction, i.e. in the direction opposite the unlocking direction. In this position, the flexible arm extends generally parallel with the longitudinal axis. Thus a robust locking mechanism is provided.

Figure 16:
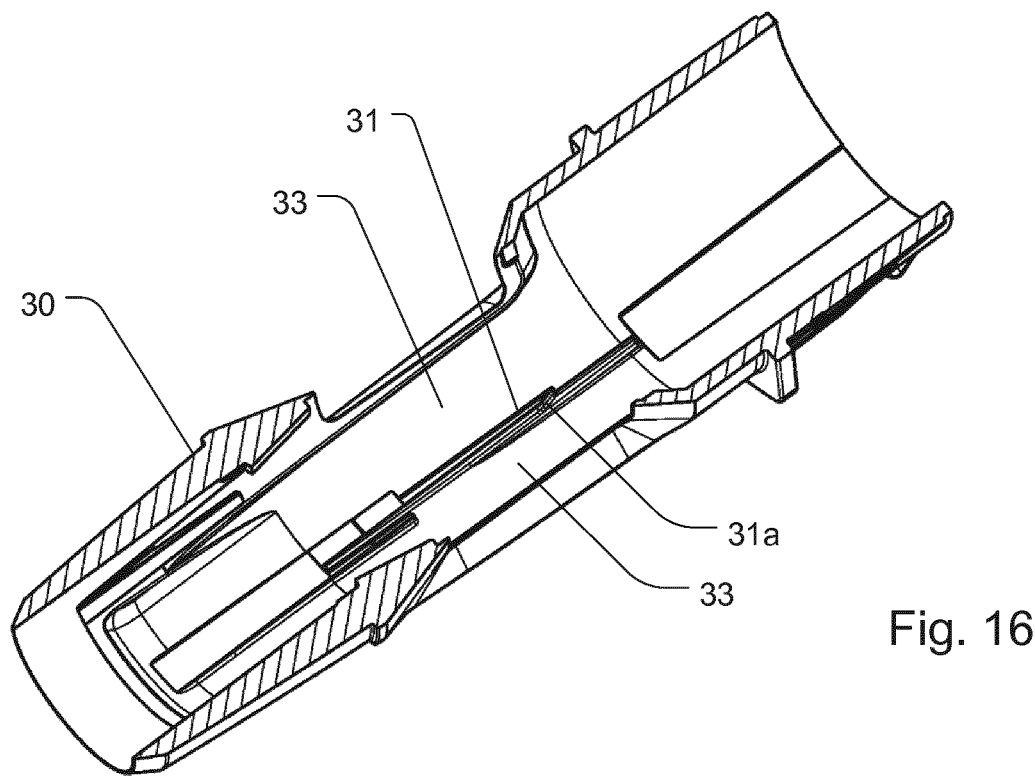
FIG. 16 shows a perspective partial section view of a housing of an injection device.

FIG. 16 shows a view of lower housing section 30 wherein ramp element 31 at its proximal end exhibits a surface 31a that is angled so as to interface with surface 24a of the flexible arm 24 of the needle hub 21. Surfaces 24a and 31a are formed with an inclination so as to impart a sideways force on the distal end of flexible arm 24 as the needle hub 21 is inserted distally relative to the housing 30.

Figure 17:
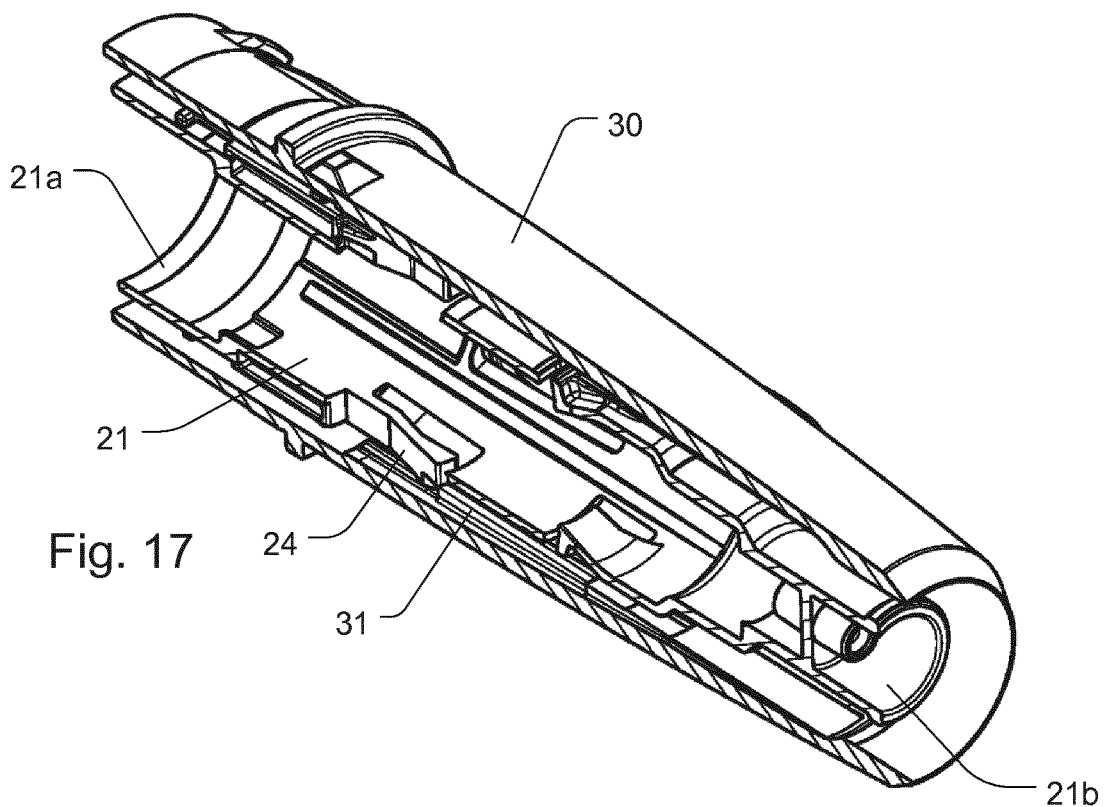
FIG. 17 shows a perspective partial section view of the needle hub of FIG. 15 inserted into the housing of FIG. 16 in a locked position, but without the needle shield, needle or cover elements being shown.
Figure 18:
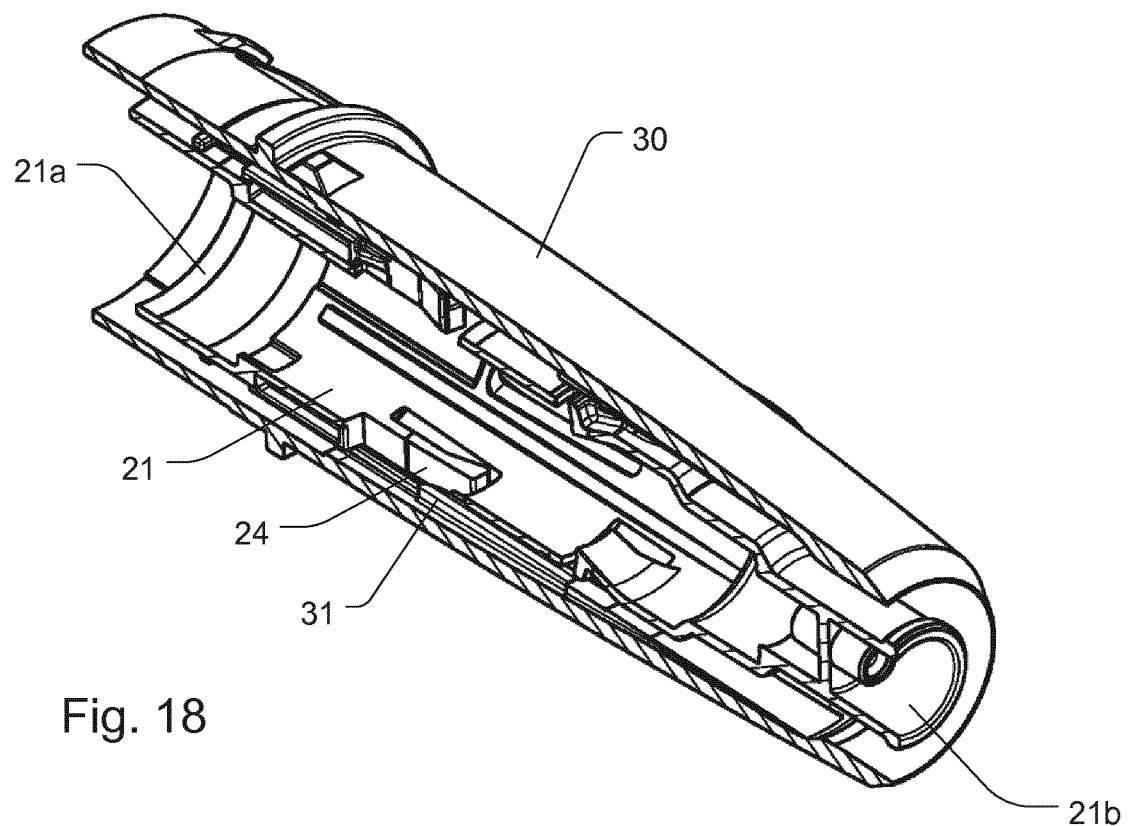
FIG. 18 shows a perspective partial section view of the needle hub of FIG. 15 inserted into the housing of FIG. 16 in an unlocked position, again without the needle shield, needle or cover elements being shown.

FIG. 17 shows a perspective partial section view of the needle hub of FIG. 15 inserted into the housing of FIG. 16 in a locked position. Again, the needle shield, the needle and the cover elements are omitted from the view, cf. to FIG. 10. In FIG. 17, one can see the free end of the flexible arm 24 just engaging the end of the ramp element 31, i.e. the first surface 24a engages surface 31a. As the needle hub is pressed further into the housing, the inclination of the first surface 24a of the flexible arm and the inclination of surface 31a of the ramp element 31 causes the free end of the flexible arm 24 to be pushed more to the side in the unlocking direction as shown in FIG. 18 where the arm has been completely displaced to the side.

Figure 19:
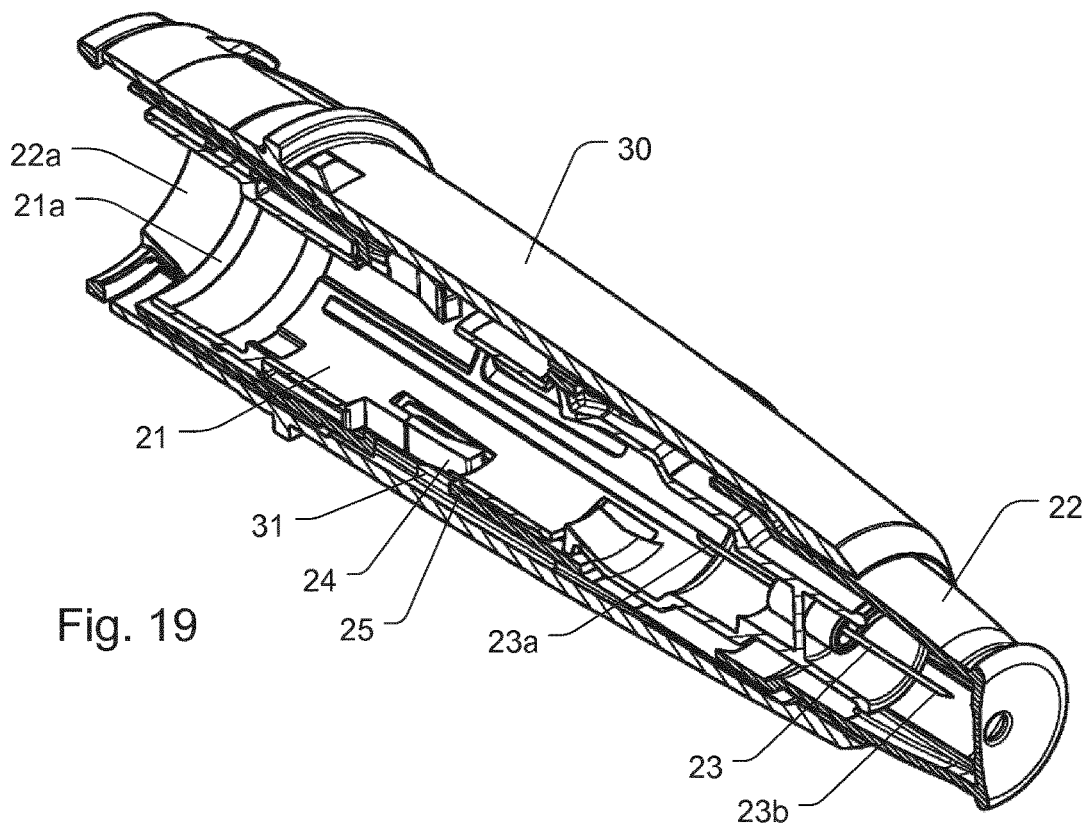
FIG. 19 shows a second perspective partial section view of the components of FIG. 18, but with the needle shield and the needle also shown.
Figure 20:
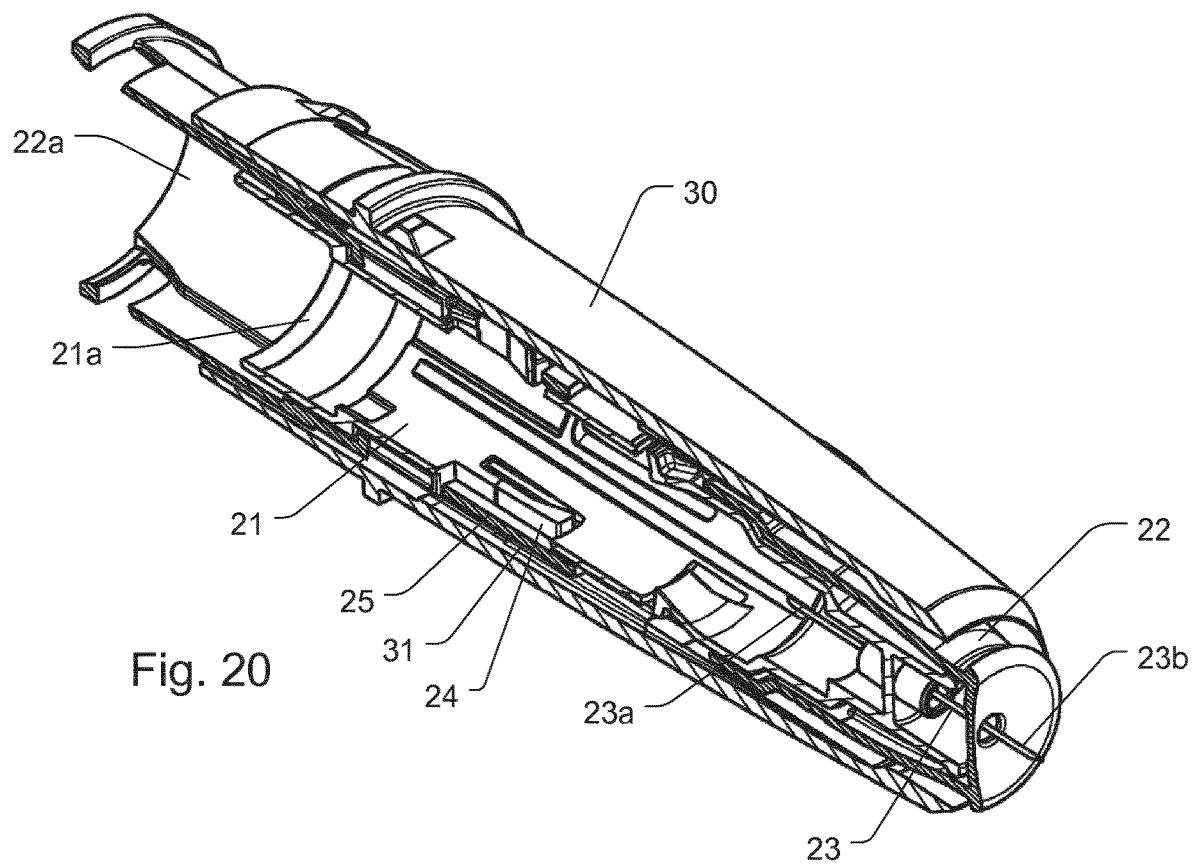
FIG. 20 shows a perspective partial section view of the view of FIG. 19, but with the needle shield retracted to expose the needle.

FIGS. 19 and 20 now include the needle shield 22 and the needle 23. In FIG. 19 it can be seen that the free end of the arm 24 has been pushed so far to the side, that it is no longer engaged with the end of the first step of the stepped slot 25. As such the needle shield can now be displaced further towards the proximal end of the device. This is shown in FIG. 20 where the needle shield has been pushed towards the proximal end thereby exposing the distal end 23b of the needle 23. In this position the needle shield cannot be displaced further in a proximal direction with respect to the needle hub.

It is to be noted that the figures and the above description have shown and described the example embodiments without describing each individual feature shown in the drawings. Furthermore, many of the details have not been described in detail since the person skilled in the art should be familiar with these details and they would just unnecessarily complicate this description.

Furthermore, some preferred embodiments have been shown in the foregoing, but it should be stressed that the invention is not limited to these, but may be embodied in other ways within the subject matter defined in the following claims.

The invention claimed is:

1. A needle unit for cooperation with an injection device comprising a housing and a lock release element, the needle unit comprising:
   an injection needle assembly comprising a needle hub and a needle gripped by the needle hub, the needle having a proximal end, a distal end and a longitudinal axis extending between the proximal and distal ends, and
   a needle shield having a proximal end and a distal end,
   wherein the injection needle assembly and the needle shield are arranged to form the needle unit where the injection needle assembly is arranged displaceably inside the needle shield such that the injection needle assembly is displaceable along an axis which is parallel with the longitudinal axis of the needle between a shielded position where the distal end of the needle shield extends distally past the distal end of the needle and where the proximal end of the needle shield and/or the needle hub extend(s) proximally past the proximal end of the needle and an exposed position where the distal end of the needle extends distally past the distal end of the needle shield,
   wherein the needle unit further comprises, a penetrable cover element at the proximal end and distal end of the needle, forming a sterility seal that seals off the needle from the needle hub, characterized in that
   the needle hub comprises a first hub locking element and a second hub locking element and in that the needle shield further comprises a first shield locking element and a second shield locking element,
   said first hub locking element and said first shield locking element engaging each other in the shielded position to establish a releasable first locking mechanism between the needle hub and the needle shield which when locked prevents the distal end of the needle from displacing in a distal direction with respect to the needle shield,
   said second hub locking element and said second shield locking element engaging each other in the shielded position to establish a second locking mechanism between the needle hub and the needle shield to prevent the proximal end of the needle from displacing in a proximal direction with respect to the needle shield,
   both the first and second locking mechanisms being arranged as shock proof locks, and wherein the releasable first locking mechanism is arranged to engage with the lock release element of the injection device when the needle unit is coupled to the injection device, said engagement allowing the releasable first locking mechanism to be unlocked.

2. A needle unit according to claim 1, wherein each penetrable cover element at the proximal end and distal end of the needle is configured as a collapsible penetrable boot that, when an axial compression force acts on the cover element, the boot collapses causing the needle to pierce and penetrate the cover element.

3. A needle unit according to claim 1, characterized in that the releasable first locking mechanism and the second locking mechanism are arranged as two independent locking mechanisms.

4. A needle unit according to claim 1, characterized in that the needle hub and the needle shield are provided with rotation preventing elements which prevent the needle hub and the needle shield from rotating with respect to each other around the longitudinal axis of the needle.

5. A needle unit according to claim 1, characterized in that the releasable first locking mechanism and/or the second locking mechanism are arranged proximally to the proximal end of the needle.

6. A needle unit according to claim 1, characterized in that the releasable first locking mechanism is unlocked via an outer side of the needle shield.

7. A needle unit according to claim 6, characterized in that the needle shield comprises an opening in a side of the needle shield through which the releasable first locking mechanism is unlockable.

8. A needle unit according to claim 1, characterized in that the releasable first locking mechanism is arranged to automatically unlock when the needle unit is coupled to the housing of the injection device.

9. An injection device comprising a needle unit according to claim 1, the injection device comprising a housing and a lock release element, characterized in that the lock release element of the injection device is arranged as a fixed portion of the housing of the injection device and that the releasable first locking mechanism is arranged to automatically unlock when the needle unit is coupled to the housing.

10. An injection device according to claim 9, characterized in that the lock release element is a ramp element and the first hub locking element and/or the first shield locking element are arranged to be displaced by the ramp element to unlock the releasable first locking mechanism when the needle unit is coupled to the injection device.

11. A method of manufacturing an injection device, the manufactured injection device comprising a needle shield having a proximal end and a distal end, a needle hub and a housing, said needle hub comprising a needle having a distal end, a proximal end and a longitudinal axis extending from the distal end to the proximal end, the needle hub and the needle shield being movable axially relative to each other for shifting the needle from a shielded state to an exposed state, said needle shield being arranged such that in the shielded state, the proximal end of the needle shield extends proximally past the proximal end of the needle and the distal end of the needle shield extends distally past the distal end of the needle and that in the exposed state the distal end of the needle extends distally past the distal end of the needle shield, the method comprising the steps of:
   providing a needle hub, the needle hub comprising a first hub locking element,
   providing a needle shield, the needle shield comprising a first shield locking element configured to cooperate with the first hub locking element,
   securing the needle hub and the needle shield relative to each other to form a needle unit wherein the needle is in the shielded state, the needle unit further comprising a penetrable cover element at the proximal end and distal end of the needle, forming a sterility seal that seals off the needle from the needle hub,
   moving the first hub locking element and the first shield locking element relative to each other to establish a first releasable locking mechanism between the needle hub and the needle shield which prevents the needle from being shifted into the exposed state by displacement of the needle relative to the needle shield in a distal direction, the first releasable locking mechanism being arranged as a shock-proof lock,
   providing a housing, and
   assembling the needle unit with the housing and moving the first hub locking element and the first shield locking element relative to each other to release the first releasable locking mechanism for enabling axial movement between the needle shield and the needle hub to allow the distal end of the needle to be exposed.

12. The method according to claim 11, characterized in that the step of assembling the needle unit with the housing further comprises the step of releasing the first releasable locking mechanism by positioning the needle unit relative to the housing whereby a release geometry on the housing releases the first releasable locking mechanism.

13. The method according to claim 11 characterized in that the method further comprises the steps of:
   providing a needle shield release button, the needle shield release button comprising a release geometry configured to operate and release the first releasable locking mechanism, and
   assembling the needle shield release button with a housing section and the needle unit.

14. The method according to claim 11, wherein the first releasable locking mechanism is so configured that release of the first releasable locking mechanism requires relative movement of at least one of the first hub locking element and the first shield locking element in a direction which is not parallel with the longitudinal axis of the needle.

15. The method according to claim 11, characterized in that said method further comprises the step of sterilizing the needle unit, subsequent to the step of moving the first hub locking element.

* * * * *